United States Patent [19]

Elliott

[11] Patent Number: 5,620,695
[45] Date of Patent: Apr. 15, 1997

[54] METHOD AND COMPOSITION FOR TREATING MINOR SKIN IRRITATIONS

[76] Inventor: Jennifer Elliott, 12495 148th Rd. North, Palm Beach Gdns, Fla. 33418

[21] Appl. No.: 647,723

[22] Filed: May 13, 1996

[51] Int. Cl.$^6$ ..................................... A61K 7/48
[52] U.S. Cl. .......................... 424/405; 424/401; 514/817; 514/887
[58] Field of Search ................................... 424/401, 405; 514/817, 887

[56] References Cited

U.S. PATENT DOCUMENTS

| | | | |
|---|---|---|---|
| 4,235,873 | 11/1980 | Packman | 424/47 |
| 5,385,733 | 1/1995 | Mankovitz | 424/195.1 |
| 5,417,961 | 5/1995 | Nearn et al. | 424/59 |
| 5,431,924 | 7/1995 | Ghosh et al. | 424/522 |

Primary Examiner—Thurman K. Page
Assistant Examiner—Diedra Faulkner
Attorney, Agent, or Firm—McHale & Slavin, P.A.

[57] ABSTRACT the instant invention is a method and composition for the treatment of minor skin irritations based upon the use of a carrier oil with the essential oils of eucalyptus, lavender and ti tree added to the oil with a most unique composition capable of reducing the irritation, promoting healing, resisting insects, and take advantage of the science of aromatherapy.

7 Claims, No Drawings

METHOD AND COMPOSITION FOR TREATING MINOR SKIN IRRITATIONS

FIELD OF THE INVENTION

This invention relates to a method and composition for treating a wide variety of skin irritations with particular application to animals and has been especially effective on horses.

BACKGROUND OF THE INVENTION

Skin irritation problems are numerous and common. They can develop from weather conditions (from dying to sunburn, fungal infections from dampness and windburn), generalized itching insects such as horse flies, deer flies, gnats, mosquitoes, sea lice and ants, as well as accidents and injuries.

Some medicated skin lotions are known in the art, however most are one use specific, require a medical diagnosis or aseptic technique in application and are either costly or have many side effects, particularly on an animal that is outdoors much of the time.

SUMMARY OF THE INVENTION

Disclosed is a novel, topical skin lotion capable of stopping the itching and discomfort, calming the skin, repelling insects and speeding the healing process. It has a wide range of applications, requires no physician or veterinarian prescription and can be used by the layman under all conditions.

The lotion is a mixture of carrier oil and essential oils of lavender, eucalyptus, and ti tree oils. PABA can be added as sunscreen. While each ingredient is know in the art, the combination and formulation has not been disclosed in the prior art.

This lotion provides antiseptic and antibiotic properties to inhibit infection, has soothing and calming qualities to decrease the irritation and prevent animals from scratching further, repels insects which decreases infection and itching, cools and irritation and speeds healing. Its advantages are: it easy to apply and will benefit almost any skin irritation, it has no known side effects, it is all natural, its odor repels insects, it is not changed or rendered ineffective in any weather conditions, it can be applied by hand with non-sterile technique and the type, qualify and composition of all ingredients are considered safe by human standards, and indeed, are often used in massage creams by professionals.

DETAILED DESCRIPTION OF THE PREFERRED EMBODIMENT

Although the invention is described in terms of a specific embodiment, it will be readily apparent to those skilled in this art that various modifications, rearrangements, and substitutions can be made without departing from the spirit of the invention. The scope of the invention is defined by the claims appended hereto.

The instant invention is a composition and method for treating minor skin irritations. Based in a carrier, certain ingredients provide a composition capable of treating skin irritations in such a manner so as to soothe the irritation while promoting healing. The basis of the composition is a neutral carrier oil, having no additives or properties that would inhibit healing or develop side effects, to support the primary ingredients. The essential oils are added to the carrier oil and thoroughly mixed. The recommendation is that, when used over large areas, the animal be washed thoroughly with anti-fungal shampoo prior to application. On smaller areas, this is not necessary. Essential oils are extracts (usually through the steam distillation process) of flowers and plants in a highly concentrated form. Essential oils are used extensively in foods (especially natural flavorings such as lemon and peppermint), cosmetics (perfumes and skin care) and medicines. Essential oils are used externally and internally in medical settings throughout England and Europe.

Essential oils are usually added to a carrier oil, like canola, that serves as a stabilizing and diluting base the encourages absorption in addition to coating the skin. *Lavendula angustifola* (lavender) is considered the most useful and most versatile therapeutically of all the essential oils and is effective on almost all skin conditions. It is considered antiseptic, antibiotic, analgesic and anti-inflammatory. It also has been used historically as an insect repellent. Research found that it is cytophylactic—i.e., it encourages skin cell regeneration. It is considered safe enough to use on human infants. It has the additional emotional effects of calming emotions and nervous tension *Eucalyptus globulus* cools the skin. Its odor repels insects. It is anti-inflammatory and highly effective on fungal infections. It was used in World War II as an antiseptic. Ti tree, also spelled tea tree but correctly names Melaleuca Alternifolia has the unusual properties of being antifungal, antiviral and antibacterial.

Essential oils are unique when compared to modern American medicines, in that they have many properties and therefore are multi-functional for a variety of ills. Additionally effectiveness is multiplied when special oils are used together.

| The composition consists of: |
| --- |
| 96% carrier oil |
| 2% lavender |
| 1% eucalyptus |
| 1% ti tree |

For example, a composition may be prepared by using 128 ounces of canola oil as the carrier, admixing about 2.5 ounces of lavender into the carrier oil; admixing about 1.25 ounces of eucalyptus into the carrier oil; and admixing about 1.25 ounces of ti tree into the carrier oil. The mixture is applied topically to the skin. Preferably, the skin is first washed with an anti-fungal shampoo. PABA may be added as a sunscreen at a rate of ¼ cup per gallon, adding of PABA will require the application of heat.

For a horse, the composition is applied sparingly to ears and face, and liberally to the coat, mane and tail at least once per day until the itching stops and then only as needed.

It is to be understood that while I have illustrated and described certain forms of may invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A composition for treating minor skin irritations comprising: about 96% fluid carrier oil; about 2% of lavender; about 1% of eucalyptus; and about 1% of ti tree.

2. The composition of application according to claim 1, wherein said carrier is vegetable oil.

3. The composition of application according to claim 1, wherein said carrier is canola oil.

4. The composition of application according to claim 1 including PABA.

5. A method of treating minor skin irritations and the method of making one gallon of solution for treating minor skin irritations comprising the steps of:

admixing about 2.5 ounces of lavender into a carrier oil;

admixing about 1.25 ounces of eucalyptus into said carrier oil;

admixing about 1.25 ounces of ti tree into said carrier oil;

washing the skin irritation with an anti-fungal shampoo; and coating the skin irritation with said carrier oil.

6. The method of application according to claim 5 wherein said carrier oil is defined as canola oil.

7. The method of application according to claim 5 including about 8 ounces of PABA.

* * * * *